United States Patent [19]

Carlsson et al.

[11] 4,296,760
[45] Oct. 27, 1981

[54] ELECTRICAL STIMULATOR

[75] Inventors: Per-Olov A. V. Carlsson, Sosdala; Bo H. Hakansson, Lund, both of Sweden

[73] Assignee: Gambro AB, Sweden

[21] Appl. No.: 97,380

[22] Filed: Nov. 26, 1979

[30] Foreign Application Priority Data

Nov. 27, 1978 [SE] Sweden .............................. 7812159

[51] Int. Cl.³ .............................................. A61N 1/04
[52] U.S. Cl. .................................................. 128/788
[58] Field of Search ............... 128/130, 131, 251, 788, 128/783, 246

[56] References Cited

U.S. PATENT DOCUMENTS

| | | | |
|---|---|---|---|
| 3,708,268 | 10/1963 | Uttal .................................... | 128/783 |
| 3,754,553 | 8/1973 | Hewitt et al. ........................ | 128/251 |
| 4,106,511 | 8/1978 | Erlandsson ........................... | 128/788 |

FOREIGN PATENT DOCUMENTS

217090 12/1909 Fed. Rep. of Germany ...... 128/788

*Primary Examiner*—William E. Kamm
*Attorney, Agent, or Firm*—Lerner, David, Littenberg & Samuel

[57] ABSTRACT

Electrical stimulators are disclosed particularly for vaginal placement, comprising an element which is elongated along an axis corresponding with a direction in which the stimulator is intended to be placed, and, including a transverse cross-section having elongated axis in one direction perpendicular to its other axis, and a plurality of electrodes located on one side of a longitudinal cross section of the elongated element corresponding with that elongated axis, thus stabilizing its rotation upon its vaginal placement with the electrodes facing in a predetermined direction. The electrodes are adapted to control the urethral, urocystic and/or rectal functions through electrical pulses provided from a pulse generator, and the elongated element is preferably formed of rubber, plastics or the like, and is inflatable.

13 Claims, 7 Drawing Figures

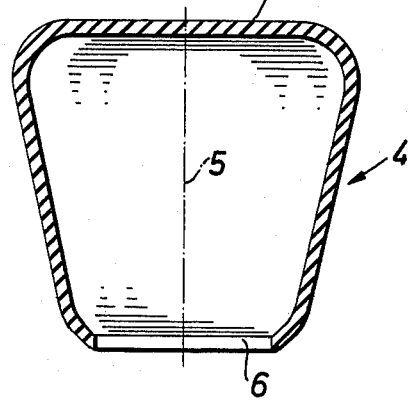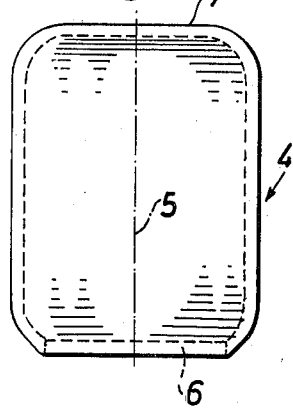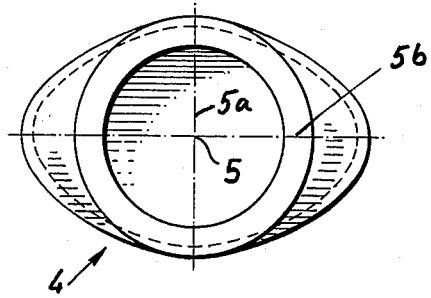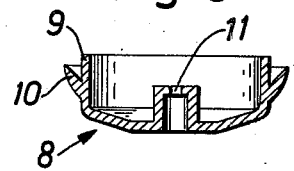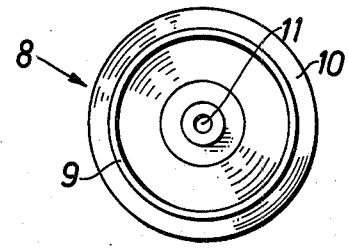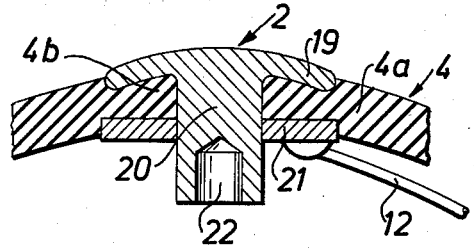

ELECTRICAL STIMULATOR

FIELD OF THE INVENTION

The present invention relates to an electrical stimulator, particularly for vaginal placement. More particularly, the present invention relates to electrical stimulators carrying two or more electrodes with are adapted to control the urethral, urocystic and/or rectal functions through electrical pulses from a pulse generator.

BACKGROUND OF THE INVENTION

Disturbances in the urinary and rectal functions are a great problem both for the individual person involved as well as for nursing attendants, etc. Urinary incontinence is quite common, and from a nursing point of view is very time-consuming, requiring the changing of clothing, bedding, etc.

There have been attempts to solve these problems in a number of different ways. For example, technical means for the collection of urine have been employed. These work tolerably well in the case of men, but are much more difficult to realize with women.

There have also been attempts to electrically stimulate the pelvis floor through the implantation of electrodes in the pelvis floor musculature. These electrodes are then connected to a pulse generator which is placed subcutaneously, and which can in turn be supplied e.g. electromagnetically, with pulses from a transmitter placed outside the body. This method, however, requires surgical intervention, and is relatively complicated and costly. Examples of such implantable devices are disclosed in U.S. Pat. Nos. 3,543,761; 3,667,477 and 3,870,051.

In another method contraction of the urethra is achieved by means of electrical stimulation by means of electrodes arranged on an element carried intravaginally or anally. Generally, however, elements of this type are made of a rigid plastic material of circular cross-section, and the electrodes frequently constitute peripheral metal rings. Examples of such devices are set forth in British Pat. No. 1,286,075 and in U.S. Pat. No. 3,943,938. Apart from the discomfort associated with the wearing of such a hard element inside the body, there is also a risk of it sliding out. Moreover, a stimulation of the whole pelvis region is obtained through the peripheral electrodes, and this is not always appropriate.

In U.S. Pat. No. 4,106,511, an improved design of a stimulator is described. This electrical stimulator, which is intended for vaginal or anal placement, comprises an element consisting of a flexible material which is expandable so as to achieve secure attachment in the body. The element disclosed in this patent is provided with a substantially planar end wall at its inner end in its applied position. This end wall is intended to facilitate placing and retention of the element in the desired position. In spite of the fact that the element in this patent has a shape which is not quite rotational-symmetrical, there is a great risk of its turning, and as a result two groups of electrodes may point in an incorrect direction, and thus obtain an undesirable direction of stimulation. This tendency of spinning away from the desired position is initially due to the fact that the electrodes are placed opposite one or more protuberances which are intended to facilitate the maintainance of the element in a selected vaginal or anal position. However, a normal vagina has a cross-sectional shape which includes a dimension at right angles to the longest dimensions of the cross-sections of the known element which is longer than those dimensions, and therefore there is a resulting tendency for the device to spin or turn.

It is therefore an object of the present invention to provide an electrical stimulator for vaginal placement which in particular has an improved design compared with those of the prior art, such as that of U.S. Pat. No. 4,106,511, which in spite of its disadvantages is probably the best of its kind produced up to now.

SUMMARY OF THE INVENTION

In accordance with the present invention, it has been discovered that these and other objects can be accomplished by employing an electrical stimulator which has a shape that is not rotationally symmetrical. In particular, the electrical stimulator of this invention comprises an elongated element which is adapted for vaginal placement and which is elongated along an axis corresponding with a direction in which the stimulator is intended to be placed. The elongated element has a transverse cross-section which has first and second perpendicular axes, and where the first axis is substantially elongated as compared to the second axis, and the elongated element includes a plurality of electrodes located on the surface of the elongated element on one side of a longitudinal cross-section of the elongated element corresponding with the first axis of its transverse cross-section. In this manner the elongated element is stabilized against rotation upon its vaginal placement with the electrodes facing in a predetermined direction, preferably in an oblique forward-upward direction. In this manner risk of the element rotating during application and thus directing the stimulations or parts which are not intended to be stimulated, is substantially eliminated. In this connection it should thus be noted that it has been asserted, for example, that electrical pulses which are intended to control the urethral or urocystic functions may instead control the rectal function if they are pointed in the wrong direction, even if vaginally placed.

In a preferred embodiment of the invention, the elongated element has a substantially oval transverse cross-section, and preferably where the substantially oval transverse cross-section, which most preferably has an increasing area taken in the direction in which the stimulator is intended to be placed. In this manner retention of the device in the desired position with additional security is achieved.

In another embodiment of the present invention, the surface of the elongated element corresponding with the first axis of its transverse cross-section and the surface of the elongated element corresponding with the second axis of its transverse cross-section have arcuate configurations, and the degree of curvature of the surface of the elongated element corresponding with the first axis is less than the degree of curvature of the surface of the elongated element corresponding with the second axis. The two surfaces which thus have a lesser degree of curvature can be said to constitute the plane sides of this component, and the electrodes are appropriately arranged on one of those surfaces which is automatically fixed in the vagina in a predetermined manner. In this manner it is again insured that the electrodes are effective in the intended direction.

In another embodiment of the present invention, the elongated element is inflatable, and preferably comprises a bladder prepared from an expandable material such as rubber, plastics or the like. In this manner both introduction of the element is facilitated and its retention is further improved.

In accordance with this embodiment of the present invention, it is preferred that the elongated element includes an opening at one end thereof corresponding with its longitudinal axis, and the stimulator further includes a cover member both for closing that opening, the opening and the cover member both being rotationally symmetrical. Preferably, this cover member includes an apeture which permits the introduction of leads into the interior of the elongated element for connection with the electrodes and furthermore for connecting the inflatable elongated element with means for inflating same, such as the connection of a tube for inflation and/or evacuation thereof. This facilitates the manufacture of the element itself and at the same time allows it to be made impermeable to gas and liquids.

In another embodiment of the present invention, the electrodes employed have a rivet-like configuration including a head for location on the surface of the elongated element, a shank projecting from the head for passage through a wall of the elongated element, and a plate projecting from the shank so that the wall of the elongated element can be clamped between the head and the plate of the electrode for firmly affixing the electrode thereto. The firmness or tightness of this affixing can be further improved by providing the heads and/or the plates with a dish-shaped configuration facing towards the wall of the element. The aforementioned leads are suitably attached to the plates.

In this embodiment of the present invention the shanks on the rivet-like electrodes preferably include a hollow end at the end of the shank displaced from the head in order to facilitate assembling of these electrodes. Control of the assembly of these elements is quite important so as to be able to insure tightness or sealing of this entire configuration. Such sealing can be further improved by including on the cover member a first flange for insertion into the opening and a second flange extending radially outwardly from the first flange so to engage the surface of the elongated element surrounding the opening upon closing the apeture with the cover member. The second flange will thus preferably having a conical configuration so as to surround the opening or mouth of the bladder in a tight manner.

It should thus be particularly noted that the degree of tightness of the elements of this electrical stimulator is of extreme importance. Thus, if this element is not impermeable to liquid the penetration of liquid can lead to the formation of bacterial centers therein. Furthermore, if it is not impermeable to gases the enclosed gas will be rapidly squeezed out of the element and thus reduce its retention raising the risk either of alteration of the direction of stimulation or the element dropping from the patient altogether.

BRIEF DESCRIPTION OF THE DRAWINGS

The invention is described in more detail below with reference to the enclosed drawings, in which FIG. 2 shows a longitudinal cross-section through the bladder (elongated element) forming part of the stimulator of the present invention prior to attachment of the electrodes thereto;

FIG. 3 shows a perspective side view of the bladder shown in FIG. 2, as seen in the direction of another longitudinal cross-section thereof;

FIG. 4 shows a bottom, perspective view of the bladder shown in FIG. 2;

FIG. 5 shows a side, cross-sectional view of an end piece or cover member for use with the bladder shown in FIG. 2;

FIG. 6 shows a top, perspective view of the cover member shown in FIG. 5, and

FIG. 7 shows a partial cross-sectional side view of a rivet-like electrode forming part of the electrical stimulator of the present invention.

DETAILED DESCRIPTION

Figure 1:
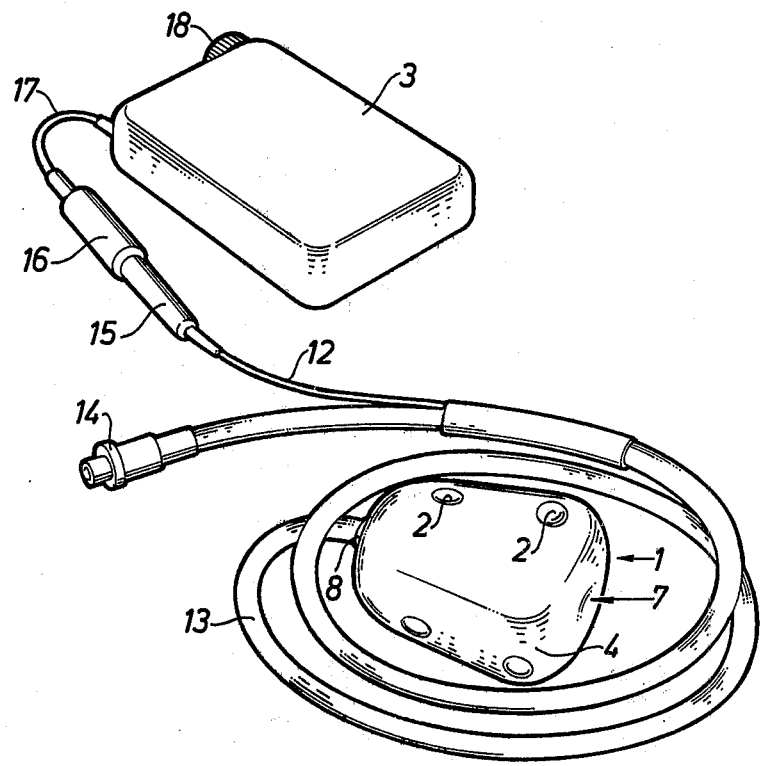
FIG. 1 shows a perspective view of the electrical stimulator of the present invention.

The preferred embodiment as shown in FIG. 1 of the stimulator in accordance with the present invention thus comprises an elongated element intended in particular for vaginal placement, which as a whole is designated by the numeral 1. In the embodiment shown this element carries four electrodes 2 which are adapted so as to control, through electrical pulses from a pulse generator 3, the urethral, urocystic and/or rectal functions.

An essential feature of this invention is in connection with the shape of the elongated element 1, which substantially consists of a bladder 4 made of rubber, plastics or some other expandable material. At the same time the element must also be completely tight, or impervious to liquids and gasses. A specific example of a material that can be employed as the bladder is a thermoplastic rubber marketed under the name of KRATON by Dry Color AB. Alternatively, silicone rubber or natural rubber may be employed.

The shape of the bladder 4 can best be seen from FIGS. 2-4. It can be said to have a longitudinal axis 5, even though its length does not necessarily have to exceed its greatest thickness. At right angles to the axis 5, the transverse cross-section is substantially oval-shaped, with a shorter axis $5a$ and a longer axis $5b$, except closest to the open mouth 6, where the cross-section is substantially circular. Thus, the longer axis $5b$ is substantially elongated as compared to the shorter perpendicular axis $5a$. The inner end of the elongated element or bladder 4 as viewed with respect to its position of application is shaped with a substantially planar end surface 7. The opposite end of the bladder 4 can be closed by end piece 8, which can be seen in more detail in FIGS. 5 and 6. End piece 8 is provided with a circular-cylindrical flange 9 which is intended to be attached inside the bladder 4, and a substantially conical flange 10 which is intended to surround the mouth or opening 6 of the bladder 4. The end piece 8 is also provided with a small opening or aperture 11 for the introduction of leads 12 connected to the electrodes 2, and for the connection of a tube 13 for the inflation and evacuation, respectively, of the element 1.

As can best be seen from FIG. 1, the tube 13 ends in a coupling component 14 which is adapted so that it can be connected to a simple hand pump or the like, for either inflation or evacuation of the element 1. In the same manner the leads 12, which in FIG. 1 are shown as a conventional two-wire cable, terminate in an electrical coupling component 15 which is joined to a second corresponding component 16, which in turn is connected to a pulse generator 3 via a cable 17. Finally, numeral 18 in FIG. 1 designates a control knob which may be adapted for the setting of the amplitude of the pulses, the pulse width and/or the frequency.

In FIG. 7 an example of the rivet-like electrodes 2 and their attachment is shown. The rivet consists of a head 10 and a shank 20. Between the head 19 and a plate 21 is clamped the wall 4a of the bladder 4. Thus, strong compression of the wall material 4b between the head 10 and the plate 21 can be realized. This ensures an effective tightness. Numeral 22 designates a recess in the end of the rivet shank 20. This recess is intended for facilitating the assembling of the rivet, as it is important that this assembling should take place in a correct manner, so as to ensure tightness. In FIG. 7 it can be seen how plate 21 is firmly fixed to the rivet. In practice, however, this is done appropriately by way of deformation of the rivet shank 20, that is to say, in a conventional manner. Finally, numeral 12 indicates how the lead 12 can be soldered firmly onto the plate 21. Alternatively, it may, of course, also be connected directly to the electrode.

It has been found in practice that the diameter of the head of the rivet-like electrode should not be less than approximately 6 mm, and not be more than approximately 12 mm. With smaller sizes there is a danger of the electrode coming loose, and if they are larger the energy consumption increases. It has also been found that the round shape of the electrodes has special advantages from a medical point of view, particularly so as to provide a better fit for different patients.

What is claimed is:

1. An electrical stimulator comprising an elongated element adapted for vaginal placement, said elongated element including a longitudinal axis, said longitudinal axis including a first end corresponding with a first end of said electrical stimulator and a second end corresponding with a second end of said electrical stimulator, said elongated element including a transverse cross-section throughout the length of said elongated element from said first end of said longitudinal axis to said second end of said longitudinal axis, said transverse cross-section having first and second perpendicular axes, said first perpendicular axis being greater than said second perpendicular axis, and a plurality of electrodes carried by said elongated element, said electrodes being located on the surface of said elongated element on one side of a longitudinal cross-section of said elongated element corresponding with said first perpendicular axis, so that when said stimulator is vaginally placed in a direction corresponding with said longitudinal axis said elongated element is stabilized against rotation with all of said electrodes facing in a predetermined direction.

2. The electrical stimulator of claim 1, wherein said transverse cross-section is substantially oval, and the area of said substantially oval transverse cross-section taken at said first end of said electrical stimulator is greater than the area of said substantially oval transverse cross-section taken at said second end of said electrical stimulator, and including continuously decreasing substantially oval cross-sections therebetween.

3. The electrical stimulator of claim 1, wherein the surface of said elongated element corresponding with said first axis and the surface of said elongated element corresponding with said second axis have arcuate configurations, and wherein the degree of curvature of said surface of said elongated element corresponding with said first axes is less than the degree of curvature of said surface of said elongated element corresponding with said second axis.

4. The electrical stimulator of claim 1, wherein said elongated element includes flexible walls, and including means for inflating said flexible walls of said elongated element.

5. The electrical stimulator of claim 4 in which said elongated element is prepared from rubber.

6. The electrical stimulator of claim 4 including an opening at one end of said elongated element corresponding with its axis, and including a cover member for closing said opening, said opening and said cover member being rotationally symmetrical.

7. The electrical stimulator of claim 6, wherein said cover member includes an aperture permitting the introduction of leads into the interior of said elongated element for connection with said electrodes and for connection with means for inflating and deflating said elongated element.

8. The electrical stimulator of claims 1 or 7, wherein said electrodes have a rivet-like configuration including a head member for location on the surface of said elongated element, a shank member projecting from said head member for passing through a wall of said elongated element, and a plate member projecting from said shank member so that said wall of said elongated element can be clamped between said head member and said plate member for firmly affixing said electrode thereto.

9. The electrical stimulator of claim 8, wherein said head member has an arcuate configuration extending towards said wall of said elongated element to assist in retaining said electrode in place.

10. The electrical stimulator of claim 8, wherein said shank member includes a hollow end portion at the end of said shank member displaced from said head member.

11. The electrical stimulator of claim 6, wherein said cover member includes a first flange for insertion into said opening and a second flange extending radially outwardly from said first flange so as to engage the surface of said elongated element surrounding said opening upon the closing of said opening with said cover member.

12. The electrical stimulator of claim 11, wherein said second flange has a conical shape.

13. The electrical stimulator of claim 4 in which said elongated element is prepared from plastic.

* * * * *